US006458792B1

(12) United States Patent
Karabelas et al.

(10) Patent No.: US 6,458,792 B1
(45) Date of Patent: Oct. 1, 2002

(54) COMPOUNDS

(75) Inventors: Kostas Karabelas; Peter Sjö, both of Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/297,543

(22) PCT Filed: Feb. 26, 1999

(86) PCT No.: PCT/SE99/00275
§ 371 (c)(1),
(2), (4) Date: May 3, 1999

(87) PCT Pub. No.: WO99/46264
PCT Pub. Date: Sep. 16, 1999

(30) Foreign Application Priority Data

Mar. 13, 1998 (SE) .............................. 9800835

(51) Int. Cl.[7] ..................... A61K 31/498; C07D 403/04
(52) U.S. Cl. ...................... 514/250; 544/344
(58) Field of Search .................... 544/344; 514/250

(56) References Cited

U.S. PATENT DOCUMENTS

| | | | |
|---|---|---|---|
| 3,642,803 A | 2/1972 | Welstead, Jr. ........ 260/293.61 |
| 3,821,389 A | 6/1974 | Grivas .................... 424/270 |
| RE28,973 E | 9/1976 | Welstead, Jr. ........ 260/293.61 |
| 4,031,221 A | 6/1977 | Helsley et al. ........... 424/267 |
| 4,062,869 A | 12/1977 | Weston .................. 260/326.16 |
| 4,466,976 A | 8/1984 | Klose et al. ............. 424/273 |
| 4,532,250 A | 7/1985 | Stout et al. ............. 514/341 |
| 4,585,771 A | 4/1986 | Klose et al. ............. 514/220 |
| 4,598,079 A | 7/1986 | Beyerle et al. .......... 514/252 |
| 4,912,125 A | 3/1990 | Huebner et al. ......... 514/402 |
| 5,057,614 A | 10/1991 | Davis et al. ............. 548/466 |
| 5,077,293 A | 12/1991 | Smith et al. ............. 514/253 |
| 5,192,770 A | 3/1993 | Clark et al. ............. 514/305 |
| 5,380,746 A | 1/1995 | Barth et al. ............. 514/414 |
| 5,399,712 A | 3/1995 | Hill ........................ 578/455 |
| 5,466,699 A | 11/1995 | Robertson et al. ....... 514/323 |
| 5,516,915 A | 5/1996 | Barth et al. ............. 548/455 |
| 5,545,636 A | 8/1996 | Heath et al. ............. 514/214 |
| 5,612,362 A | 3/1997 | MacLeod ................ 514/392 |
| 5,668,152 A | 9/1997 | Heath, Jr. et al. ....... 514/323 |
| 5,948,907 A | 9/1999 | Faul et al. ............... 540/469 |
| 6,015,807 A | 1/2000 | Engel et al. ............. 514/183 |
| 6,054,590 A | 4/2000 | Poindexter et al. ..... 543/311.1 |
| 6,153,641 A | 11/2000 | Bergstrand et al. ...... 514/414 |

FOREIGN PATENT DOCUMENTS

| | | |
|---|---|---|
| DE | 3141063 A1 | 4/1983 |
| EP | 0328026 A1 | 2/1989 |
| EP | 0464604 A2 | 1/1992 |
| EP | 0490263 A1 | 6/1992 |
| EP | 0540956 A1 | 11/1993 |
| EP | 0675125 A1 | 10/1995 |
| FR | 7311450 | 3/1973 |
| GB | 1500176 | 2/1978 |
| SU | 389096 | 7/1973 |
| WO | WO93/18765 | 9/1993 |
| WO | WO95/17182 | 6/1995 |
| WO | WO 96/01825 | 1/1996 |
| WO | WO 98/13368 | 4/1998 |
| WO | WO 98/43632 | 10/1998 |
| WO | WO99/32483 | 7/1999 |

OTHER PUBLICATIONS

Gazit et al., "Tyrphostins. 5. Potent Inhibitors of Platelet–Derived Growth Factor Receptor Tyrosine Kinase: Structure–Activity Relationships . . .", J. Med. Chem., 1996, vol. 39, pp. 2170–2177.

Galzunov et al., "Investigation of the Riboflavine Operon of *Bacillus Subtilis* V11. Biochemical Study of Mutants Relating to Early Stages of Biosythesis" Translated from Genetika 10(11):83–92, 1974, see Chemical Abstracts vol. 82 No. 13 (1975) abstract 82817b.

Elisabete R. Pereira et al., "Synthesis and Biological Evaluation of Monoindolyl and Indolocarbazolyl Oxazolones and Imidazolones", Chem. Pharm. Bull. 45(4) 733–736, Pharmaceutical Study of Japan: 1997.

Patent Abstracts of Japan: vol. 14 No. 459 (C–767) (4402); Oct. 4, 1990.

Yuji Oikawa et al., "Synthesis of Pimprinine And Related Oxazolylindole Alakaloids From N–ACYL Derivatives Of Tryptamine And Methyl Ester By DDQ Oxidation", Heterocycles. vol. 12. No. 11, 1979.

(List continued on next page.)

Primary Examiner—Richard L. Raymond
(74) Attorney, Agent, or Firm—Fish & Richardson PC

(57) ABSTRACT

The present invention provides inhibitors of protein kinase C, of formula (I)

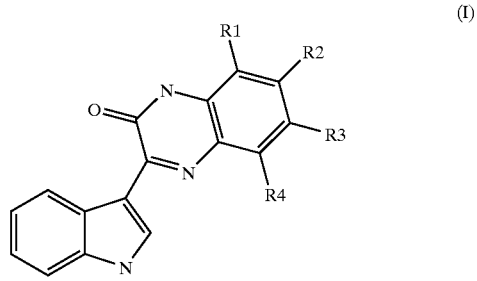

(I)

wherein:
one of: R1 and R2, R2 and R3 or R3 and R4, together form a 5 or 6 membered ring and the two groups of R1, R2, R3 and R4 not forming a ring, are H;

and salts thereof, formulations comprising said inhibitors of protein kinase C of formula (I), processes for preparation thereof and use thereof in the manufacture of a medicament for the treatment of inflammatory, immunological, bronchopulmonary, cardiovascular, oncological or CNS-degenerative disorders.

11 Claims, No Drawings

OTHER PUBLICATIONS

Carmen Galvez et al., "A Conveinent Preparation of Haloaminobenzo[b]thiophene Derivatives", Communications (932–933); Nov. 1983.

Thomas W. von Geldern et al., "Azole Endothelin Antagonists. 1. A Receptor Model Explains an Unusual Structure –Activity Profile", J. Med. Chem. 1996, 39, 957–967.

J. Bergman et al., "Synthesis And Reactions Of Some 3–(2–Haloacyl) indoles", Tetrahedron. vol. 29, pp. 971–976; Pergamon Press 1973.

Elisabete R. Pereira et al., "Syntheses and Antimicrobial Activities of Five–membered Ring Heterocycles Coupled to Indole Moietics", The Journal of Antibiotics. Apr. 1996; vol. 49 No. 4 pp. 380–385.

Bergstrand et al., "Modulation of Neutrophil Superoxide Generation by Inhibitors of Protein Kinase C, . . . ", J. of Pharm & Exp. Therap., 263:1334–1346, 1992.

Chakravarthy et al., "The Direct Measurement of Protein Kinase C (PKC) Activity in Isolated Membranes Using a Selective peptide Substrate", Analytical Biochem., 196:144–150, 1991.

Granet et al., "A Microtiter Plate Assay for Protein Kinase $C^1$", Analytical Biochem., 163:458–463, 1987.

Hauske et al., "A Solid Phase CBZ Chloride Equivalent—A New Matrix Specific Linker", Tetrahedron Letters, 36:1589–1592, 1995.

Olsson et al., "Activation of Human Neutrophil Protein Kinase C In Vitro by 1,2–Isopropylidene–3–Decanoyl–sn–Glycerol (IpOC-$COC_9$)", Cellular Signalling, 1:405–410, 1989.

COMPOUNDS

FIELD OF THE INVENTION

The present invention relates to novel compounds which are protein kinase C inhibitors, methods for their preparation, intermediates therefor and pharmaceutical compositions comprising them.

BACKGROUND OF THE INVENTION

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulphonamides, sphingosine and related sphingolipids, indolocarbazoles and bisindolylmaleimides.

Although PKC inhibitors are described in the prior art, there is a need for specific anti-inflammatory and immunosuppressive compounds which are suitable for oral administration, and for inhalation.

SUMMARY OF THE INVENTION

The present invention provides PKC inhibitors, methods for their preparation and intermediates used for their preparation.

The present invention also provides the use of the compounds of the present invention for the treatment of inflammatory, immunological, bronchopulmonary, cardiovascular, oncological or CNS-degenerative disorders.

Also provided by the present invention are pharmaceutical compositions comprising a compound according to the present invention, as active ingredient, together with a pharmaceutically acceptable adjuvant, diluent or carrier.

DETAILED DESCRIPTION OF THE INVENTION

The present invention provides optionally substituted and/or annulated compounds of formula (I):

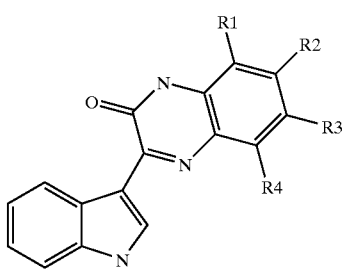

(I)

wherein:
one of: R1 and R2, R2 and R3 or R3 and R4, together form a 5 or 6 membered ring and the two groups of R1, R2, R3 and R4 not forming a ring, are H;
and salts thereof.

More specifically, the present invention provides optionally substituted and/or annulated compounds of formula (I), with the proviso that 3-[3-(3-Oxo-3,4-dihydro-benzo[g] quinoxalin-2-yl)-indol-1-yl]-propyl ammonium acetate is excluded from the compounds of formula (I).

Salts of the compounds according to the invention are preferably pharmaceutically acceptable salts. Other, non-pharmaceutically acceptable salts may be useful as intermediates e.g. in the preparation of pharmaceutically acceptable salts or other compound of the present invention.

Included within the scope of the present invention are all enol tautomers of compounds of the present invention.

Preferred compounds of formula (I) are those of formula (II):

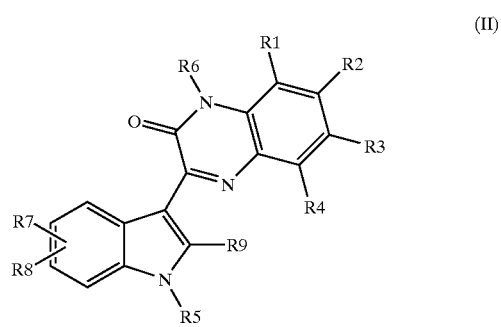

(II)

wherein:
one of: R1 and R2, R2 and R3 or R3 and R4, together form a 5 or 6 membered ring and the two groups of R1, R2, R3 and R4 not forming a ring, are H;

R5 is H, $C_{1-6}$ alkyl, hydroxy$C_{1-6}$ alkyl, amino$C_{1-6}$ alkyl, (amino$C_{1-3}$ alkylphenyl)$C_{1-3}$ alkyl, amidinothio$C_{1-6}$ alkyl, (amino$C_{1-3}$ alkylpyridyl)$C_{1-3}$alkyl;

R6 is H, $C_{1-6}$ alkyl, phenyl$C_{1-6}$ alkyl, ($C_{1-6}$ alkoxycarbonyl)$C_{1-6}$ alkyl;

R7 and R8 is each independently H, dibenzylamino, nitro, hydroxy, halogen, $C_{1-6}$ alkoxy, phenyl$C_{1-6}$alkoxy, $C_{1-6}$ alkyl or carboxy$C_{1-6}$ alkyl ester; or when R7 and R8 are adjacent they may together form amethylenedioxy;

R9 is H, $C_{1-6}$ alkyl, phenyl, halophenyl, or benzyl and wherein when R5 and R9 together comprise 3–5 carbons they may be linked to generate a cyclic moiety which may be amino$C_{1-6}$ alkyl substituted;

and salts thereof.

Compounds of formula (II), in which R5 carries an amino or hydroxy group; and pharmaceutically acceptable salts thereof, may be prepared by, a) deprotecting a compound of formula (III) corresponding to formula (II) but in which R5 carries a protected amino or hydroxy group, or b) converting:
    i) a compound of formula (II), in which R5 carries an amino group to a salt, preferably a pharmaceutically acceptable salt thereof, or vice versa; or
    ii) a salt, preferably a pharmaceutically acceptable salt of a compound of formula (II) into a different pharmaceutically acceptable salt.

Compounds of formula (II), in which R6 is hydrogen, may be prepared by reacting a compound of formula (IV):

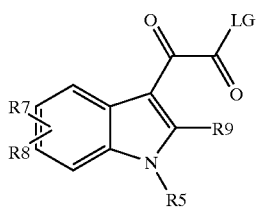

(IV)

wherein,
R5, R7, R8, and R9 are as defined in formula (II) and LG is a leaving group, e.g.:

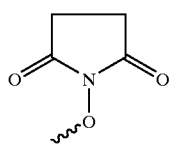

with a compound of formula (V):

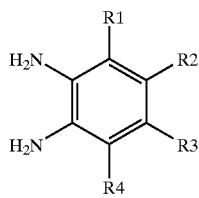

(V)

wherein,
one of: R1 and R2, R2 and R3 or R3 and R4, together form a 5 or 6 membered ring and the two groups of R1, R2, R3 and R4 not forming a ring, are H; conveniently in a solvent, e.g. tetrandrofuran (THF), at about 10–30° C., e.g. for about 16 hours.

When R5 in formula (IV) carries an amino or hydroxy group, these groups are preferably protected. The protecting groups may be removed in a subsequent deprotecting step.

Compounds of formula (II), when R6 is other than H, may be prepared by reacting a compound of formula (III) which corresponds to formula (II), but in which R6 is H, with an alkylating agent in the presence of a base, e.g. sodium hydride. The alkylating step may be carried out in a suitable solvent e.g. dimethyl formamide at about 10–30° C. for e.g. 2 hours.

When R5 in formula (III) carries an amino or hydroxy group, such groups are preferably protected. The protecting groups may be removed in a subsequent deprotecting step.

Compounds of formula (III) may be prepared by reacting a compound of formula (IV), as defined above, with a compound of formula (V), as defined above, in a solvent e.g. THF, at about 10–30° C., e.g. for 16 h ,or when R5 in formula (IV) carries an amino or hydroxy group, these are preferably in a protected form.

In all processes above, the protecting groups and conditions for deprotection are well known to those skilled in the art. Suitable protecting groups for amino groups include e.g. phthaloyl groups and the deprotecting agent may be methylamine in e.g. water. The deprotecting step may be carried out in a solvent, e.g. THF at about 10–30° C., e.g. for about 5 hours. The hydroxy groups may be protected as their corresponding acetoxy groups and the deprotecting agent may be methylamine in e.g. water. The deprotecting step may be carried out in a suitable solvent, e.g. tetrahydrofuran at about 10–30° C., e.g. for about 16 hours.

In process b) the conversion may be carried out analogously to conventional processes, e.g.
i) reaction of a free base with an acid containing the desired anion, or by careful basification of the salt, or
ii) reaction of a free acid with a base containing the desired cation, or by careful acidification of the salt.

The reaction may be carried out in a solvent, e.g. methanol ormethylene chloride.

Compounds of formula (I) which are not of formula (II) may be made by analogous processes to those described above for compounds of formula (II).

Compounds of formula (I), which are not of formula (II), carrying functional groups which might be sensitive to or interfere with the reaction conditions in the above processes, may be made by analogous processes to those described above for compounds of formula (II), but in which the functional groups are protected, followed by subsequent deprotection.

When a compounds of the present invention are synthesised as regiochemical mixtures, such mixtures may be separated by techniques well known to those skilled in the art.

Functional groups that might be sensitive for or interfere with the reaction conditions in the above processes, as well as suitable protecting groups and deprotecting methods, are evident to those skilled in the art.

Starting materials for the above processes may be made by the methods as illustrated in the Examples set out belowor by methods analogous thereto. Other methods for making the starting materials will be evident to those skilled in the art.

Compounds of formula (I) and pharmaceutically acceptable salts thereof, are useful because they demonstrate pharmacological activity. In particular they demonstrate activity as kinase inhibitors, especially PKC inhibitors, e.g. as is shown by their activity in the in vitro assays described in Granet, R. A. et al, Analyt. Biochem. 1987; 163, 458–463; Olsson, H. et al, Cell Signal 1989, 1, 405–410; Chakravarthy, B. R. et al, Analyt. Biochem. 1991, 196, 144–150 and Bergstrand, H et al, J. Pharm. Exp. Ther. 1992; 263(3), 1334–1346.

In appropriate cellular systems, compounds of formula (I) and pharmaceutical acceptable salts thereof, can also reduce the generation of inflammatory mediators. For example, the compounds can inhibit oxygen radical generation and generation of pro-inflammatory cytokines in monocytes. The compounds are especially useful as inhibitors of one or more cytokines selected from IL-1$\beta$, TNF-$\alpha$, GM-CSF or IL-8.

The compounds of the invention are indicated for use in medical therapy. More particularly, the compounds of the invention are indicated for use in the treatment of inflammatory, immunological, bronchopulmonary, cardiovascular, oncological or CNS-degenerative disorders. Preferably for oral or topical treatment of inflammatory and/or immunological disorders, such as the oral or topical treatment of airway diseases involving inflammatory conditions, e.g. asthma, bronchitis or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants.

The compounds of the invention are also indicated for use in the manufacture of a medicament for the treatment of inflammatory, immunological, bronchopulmonary, cardiovascular, oncological or CNS-degenerative disorders.

The present invention is also directed to a method for the treatment of an inflammatory, immunological, bronchopulmonary, cardiovascular, oncological or CNS-degenerative disorder, wherein a therapeutically effective amount of a compound of the invention is administered to a mammal in the need of such treatment.

The dose of the compound to be administered will depend upon the relevant indication, the age, weight and sex of the patient and may be determined by a physician. The dosage will preferably be in the range of from 0.1 mg/kg to 100 mg/kg.

The compounds may be administered topically, e.g. to the lung and/or the airways, in the form of solutions, suspensions, aerosols or dry powder formulations, e.g. formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

Compounds of the invention may be administered on their own or as a pharmaceutical composition comprising a compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The finely divided compound preferably has a mass median diameter of less than 10 $\mu$m, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

Compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or another polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatine or polyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with e.g. a vegetable oil or polyethylene glycol. Hard gelatine capsules may contain granules of the compound using either the above mentioned excipients for tablets. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

Compounds of the invention may also be administered in conjunction with other compounds used for the treatment of the above conditions.

The term 'medical therapy' as used herein is intended to include prophylactic, diagnostic and therapeutic regimens carried out in vivo or ex vivo on humans or other mammals.

Compounds of the present invention include all tautomers, stereoisomers, pure and mixed racemates, and mixtures thereof.

In compounds of formula (II) of the present invention, the following independent preferences apply:

R5 carries an amino group, when R5 and R9 together form a cyclic moiety, it is preferably a six membered ring, R2 and R3 forms a 5 or 6 membered ring, R6 is H or alkyl and is preferably H, any two adjacent R1, R2, R3 and R4 form an aromatic 6 membered ring, and any two adjacent R1, R2, R3 and R4 form a heteroaromatic 5 membered ring, preferably containing 2 nitrogen atoms.

The most preferred compounds of the present invention are as follows:

3-[1-(3-Amino-propyl)-1H-indol-3-yl]-1-benzyl-1H-benzo[g]quinoxalin-2-one trifluoroacetic acid salt, 1-(3-Amino-propyl)-3-(3-oxo-3,4-dihydro-benzo[g]quinoxalin-2-yl)-1H-indole-5-carboxylic acid methyl ester acetic acid salt, 3-[1-(3-Aminomethyl-benzyl)-5-bromo-1H-indol-3-yl]-1H-benzo[g]quinoxalin-2-one acetic acid salt, {3-[1-(3-Amino-propyl)-1H-indol-3-yl]-2-oxo-2H-benzo[g]quinoxalin-1-yl}-acetic acid methyl ester trifluoroacetic acid salt, 3-[1-(3-Amino-propyl)-1H-indol-3-yl]-1-ethyl-1H-benzo[g]quinoxalin-2-one acetic acid salt, 3-[1-(2-Amino-ethyl)-1H-indol-3-yl]-1H-benzo[g]quinoxalin-2-one acetic acid salt, 2-{3-[3-(3-Oxo-3,4-dihydro-benzo[g]quinoxalin-2-yl-indol-1-yl]-propyl}-isothiourea tris methanesufonic acid salt, 3-[1-(3-Aminomethyl-benzyl)-1H-indol-3-yl]-1,6,7,8-tetrahydro-cyclopenta[g]quinoxalin-2-one acetic acid salt, 7-[1-(3-Amino-propyl)-1H-indol-3-yl]-1,5-dihydro-1,2,5,8-tetraaza-cyclopenta[b]naphthalen-6-one acetic acid salt, 7-[1-(3-Amino-propyl)-5-bromo-1H-indol-3-yl]-1,5-dihydro-1,2,5,8-tetraaza-cyclopenta[b]naphthalen-6-one acetic acid salt, 7-[1-(3-Amino-propyl)-5-benzyloxy-1H-indol-3-yl]-1,5-dihydro-1,2,5,8-tetraaza-cyclopenta[b]naphthalen-6-one acetic acid salt, 7-[1-(3-Amino-propyl)-5-bromo-1H-indol-3-yl]-2,3-dihydro-5H-1,4-dioxa-5,8-diaza-anthracen-6-one acetic acid salt, 2-[1-(4Amino-butyl)-1H-indol-3-yl]-4H-benzo[f]quinoxalin-3-one acetic acid salt, 2-[1-(3-Aminomethyl-benzyl)-1H-indol-3-yl]-4H-benzo[f]quinoxalin-3-one acetic acid salt, 2-[1-(3-Amino-propyl)-5-bromo-1H-indol-3-yl]-4H-benzo[f]quinoxalin-3-one acetic acid salt, 3-[1-(6-Aminomethyl-pyridin-2-ylmethyl)-1H-indol-3-yl]-6,7,8,9-tetrahydro-1H-benzo[g]quinoxalin-2-one acetic acid salt, 7-[1-(3-Amino-propyl)-2-methyl-1H-indol-3-yl]-2-hydroxy-1,5-dihydro-imidazo[4,5-g]quinoxalin-6-one acetic acid salt, 2-[1-(3-Amino-propyl)-5-methoxy-1H-indol-3-yl]-4H-benzo[f]quinoxalin-3-one acetic acid salt, and the corresponding free amines thereof and other pharmaceutically acceptable salts thereof.

EXAMPLES

The following Examples illustrate, but in no way limit the invention.

All reactions were performed in dried glassware under Ar or $N_2$ unless otherwise noted. THF was distilled from sodiumibenzophenone. Dimethyl formamide (DMF) was distilled from calcium hydride, or dried over molecular sieves. Other solvents and all commercial reagents were laboratory grade and used as received.

$^1$H-NMR spectra were recorded on a Varian XL-300, Varian Unity Inova 400 or a Varian Unity Inova 500 instrument. The central solvent peaks of chloroform-d($\delta_H$ 7.27 ppm) and dimethyl sulphoxide-d$_6$ ($\delta_H$ 2.50 ppm) were used as internal references. Low-resolution mass spectra and accurate mass determinations were recorded on an Autospec-Q, Fisons Analytical, double focusing sector instrument equipped with a LSIMS interface. Low resolution mass spectra were also obtained on a Hewlett Packard 1100 LC-MS system equipped with APCI ionization chamber.

Example 1

3-[1-(6-Aminomethyl-pyridin-2-ylmethyl)-1H-indol-3-yl]-1H-benzo[g]quinoxalin-2-one Acetic Acid Salt a) {1-[6-(1,3-Dioxo-1,3-dihydro-isoindol-2-ylmethyl)-pyridin-2-ylmethyl]-1H-indol-3-yl}-oxo-acetic Acid 2,5-Dioxo-pyrrolidin-1-yl Ester 2-(6-Indol-1-ylmethyl-pyridin-2-ylmethyl)-isoindole-1,3-dione (2.70 g, 7.35 mmol) was dissolved in dichloromethane (50 ml) and cooled to 0° C. Oxalylchloride (0.63 ml, 7.35 mmol) was added and the reaction kept at 0° C. for 30 minutes before the addition of N-hydroxysuccinimide (0.85 g, 7.35 mmol) followed by careful addition of pyridine (1.19 ml, 14.7 mmol). The reaction was kept at 0° C. for 30 minutes before it was allowed to slowly regain room temperature during 3 hours and then washed with water (40 ml) and brine (2×50 ml). The organic layer was dried over $MgSO_4$ followed by removal of the solvent in vacuo to obtain the sub-title product (3.34 g, 85%).

$^1$H-NMR (400 MHz, CDCl$_3$): δ 2.94 (4H, s), 4.98 (2H, s), 5.40 (2H, s), 6.94 (1H, d, J 7.6 Hz), 7.16–7.33 (4H, m), 7.63 (1H, t, J 7.8 Hz), 7.73–7.81 (4H, m), 8.30 (1H, d, J 7.8 Hz). 8.37 (1H, s).

b) 2-{6-[3-(3-Oxo-3,4-dihydro-benzo[g]quinoxalin-2-yl)-indol-1-ylmethyl]-pyridin-2-ylmethyl}-isoindole-1,3-dione 2,3-Naphthalenediamine (0.071 g, 0.449 mmol) and the product of step a) (0.200 g, 0.373 mmol) was dissolved in tetrahydrofuran (5 ml). Stirring overnight yields 2-{6-[3-(3-Oxo-3,4-dihydro-benzo[g]quinoxalin-2-yl)-indol-1-ylmethyl]-pyridin-2-ylmethyl}-isoindole-1,3-dione as a yellow precipitate that was filtered off and washed with tetrahydrofuran/diethylether yielding the sub title product (0.151 g, 72%).

$^1$H-NMR (400 MHz, DMSO-d$_6$): d 4.87 (2H, s), 5.57 (2H, s), 7.06 (1H, t, J 7.5 Hz), 7.11 (1H, d, J 7.6 Hz), 7.21 (1H, t, J 7.4 Hz), 7.31 (1H, d, J 7.7 Hz), 7.38 (1H, d, J 8.2 Hz), 7.46 (1H, t, J 7.2 Hz), 7.52 (1H, t, J 7.2 Hz), 7.68 (1H, s), 7.71–7.78 (3H, m), 7.81–7.86 (2H, m), 7.94 (1H, d, J 8.2 Hz), 8.09 (1H, d, J 8.2 Hz), 8.48 (1H, s), 8.90 (1H, d, J 7.9 Hz), 9.03 (1H, s), 12.40 (1H, s, NH).

The product of step b) (0.142 g, 0.253 mmol) was suspended in tetrahydrofuran (3 ml) and aqueous methylamine (40%, 1.5 ml) was added. After stirring overnight the solvent was removed in vacuo. The residue was washed with water and treated with glacial acetic acid to obtain the title compound as a yellow solid (0.114 g, 92%), after freeze drying.

$^1$H-NMR (400 MHz, DMSO-d$_6$): d 1.90 (3H, s), 3.81 (2H, s), 5.67 (2H, s), 6.95 (1H, d, J 7.7 Hz), 7.29 (2H, m, J 7.0 Hz), 7.36 (1H, d, J 7.7 Hz), 7.46 (1H, t, J 7.2 Hz), 7.52 (1H, t, J 7.1 Hz), 7.57 (1H, d, J 7.1 Hz), 7.67–7.92 (2H, m), 7.94 (1H, d, J 8.3 Hz), 8.09 (1H, d, J 8.2 Hz), 8.49 (1H, s), 9.01 (1H, d, J 7.3 Hz), 9.16 (1H, s).

FAB-MS: m/z 432.1 [MH+].

Example 2

3-[1-(3-Aminomethyl-benzyl)-1H-indol-3-yl]-1H-benzo[g]quinoxalin-2-one Acetic Acid Salt The title product was prepared following the method outlined in Example 1.

$^1$H-NMR (400 MHz, DMSO-d$_6$): δ 1.98 (3H, s), 3.71 (2H, s), 5.59 (2H, s), 7.10–7.13 (1H, m), 7.25–7.35 (5H, m), 7.46 (1H, t, J 7.2 Hz), 7.52 (1H, t, J 7.4 Hz), 7.59 (1H, d, J 7.0 Hz), 7.68 (1H, s), 7.94 (1H, d, J 8.0 Hz), 8.08 (1H, d, J 8.1 Hz), 8.49 (1H, s), 9.01 (1H, d, J 7.1 Hz), 9.12 (1H, s). FAB-MS: m/z 431.1 [MH+].

Example 3

3-[1-(4-Aminomethyl-benzyl)-1H-indol-3-yl]-1H-benzo[g]quinoxalin-2-one Acetic Acid Salt The title product was prepared following the method outlined in Example 1.

$^1$H-NMR (400 MHz, DMSO-d$_6$): δ 1.88 (3H, s), 3.67 (2H, s), 558 (2H, s), 7.23–7.36 (6H, m), 7.42–7.48 (1H, m), 7.52 (1H, t, J 7.5 Hz), 7.59 (1H, d, J 7.2 Hz), 7.68 (1H, s), 7.93 (1H, d, J 8.2 Hz), 8.08 (1H, d, J 8.2 Hz), 8.48 (1H, s), 9.00 (1H, d, J 7.5 Hz), 9.12 (1H, d, J 7.5 Hz) FAB-MS: m/z 431.1 [MH+].

Example 4

3-[1-(4-Amino-butyl)-2-benzyl-1H-indol-3-yl]-1H-benzo[g]quinoxalin-2-one Acetic Acid Salt The title product was prepared following the method outlined in Example 1.

¹H-NMR (500 MHz, DMSO-d₆): δ 1.33–1.45 (4H, m), 1.87 (3H, s), 2.49 (2H, m), 4.10 (2H, t, J 7.2 Hz), 4.55 (2H, s), 7.10 (1H, t, J 7.5 Hz), 7.14–7.20 (2H, m), 7.23–7.29 (4H, m), 7.44 (1H, t, J 7.7 Hz), 7.48 (1H, d, J 8.1 Hz), 7.53 (1H, t, J 7.4 Hz), 7.68 (1H, s), 7.77 (1H, d, J 7.9 Hz), 7.94 (1H, d, J 8.4 Hz), 8.04 (1H, d, J 8.4 Hz), 8.29 (1H, s) FAB-MS: m/z 473.2 [MH+]

Example 5

3-[1-(4Amino-butyl)-1H-indol-3-yl]-1H-benzo[g]quinoxalin-2-one Acetic Acid Salt

The title product was prepared following the method outlined in Example 1. ¹H-NMR (400 MHz, DMSO-d6): δ 1.44 (2H, m), 1.83–1.88 (2H, m), 2.65 (2H, t, J 7.1 Hz), 4.36 (2H, t, J 7.0 Hz), 7.30–7.34 (2H, m), 7.44–7.54 (2H, m), 7.64–7.66 (1H, m), 7.67 (1H, s), 7.93 (1H, d, J 8.4 Hz), 8.08 (1H, d, J 7.8 Hz), 8.48 (1H, s), 9.00–9.01 (2H, m). FAB-MS: m/z 338.2 [MH+].

Example 6

1-(3-Amino-propyl)-3-(3-oxo-3,4dihydro-benzo[g]quinoxalin-2-yl)-1H-indole-5-carboxylic Acid Methyl Ester Acetic Acid Salt The title product was prepared following the method outlined in Example 1.

¹H-NMR (400 MHz, DMSO-d6): δ 1.88 (3H, s), 1.95 (2H, t, J 7.0 Hz), 2.63 (2H, m), 3.96 (3H, s), 4.46 (2H, t, J 7.0 Hz), 7.47 (1H, m), 7.54 (1H, m), 7.70 (1H, m), 7.78 (1H, d, J 8.4 Hz), 7.92–7.96 (2H, m), 8.16 (1H, d, J 8.2 Hz), 8.40 (1H, s), 9.08 (1H, s), 9.65 (1H, d, J 1.3 Hz). FAB-MS: m/z 427.2 [MH+]

Example 7

3-[1-(3-Amino-propyl)-5-dibenzylamino-1H-indol-3-yl]-1H-benzo[g]quinoxalin-2-one Acetic Acid Salt The title product was prepared following the method outlined in Example 1.

¹H-NMR (400 MHz, DMSO-d6): δ 1.88 (3H, s), 1.91 (2H, m), 2.62 (2H, t, J 7.0 Hz), 4.28 (2H, t, 7.0 Hz), 4.86 (4H, s), 6.86 (1H, dd, J 2.3, 7.0), 7.24 (2H, t, 7.2 Hz), 7.36–7.50 (11H, m), 7.59 (1H, s), 7.74 (1H, s), 7.90 (1H, m), 7.98 (1H, m), 8.35 (1H, d, J 2.4 Hz), 8.82 (1H, s). FAB-MS: m/z 564.3 [MH+]

Example 8

3-[1-(3-Amino-propyl)-1H-indol-3-yl]-6,7-dihydro-1H-cyclopenta[g]quinoxaline-2,8-dione trifluoroacetic Acid Salt a) [1-(3-tert-Butoxycarbonylamino-propyl)-1H-indol-3-yl]oxo-acetic acid 2,5-Dioxo-pyrrolidin-1-yl Ester (3-Indol-1-yl-propyl)carbamic acid tert-butyl ester (1.00 g, 3.62 mmol) was dissolved in dichloromethane (10 ml) and cooled to 0° C. followed by addition of oxalylchloride (0.32 ml, 3.72 mmol). After stirring for 30 minutes N-hydroxysuccinimide (0.42 g, 3.65 mmol) was added, directly followed by pyridine (0.6 ml, 7.45 mmol) the mixture was then stirred at room temperature for one hour. Dichloromethane (50 ml) was added and the organic phase was extracted with brine (5%, 3×25 ml), dried over Na₂SO₄ and evaporated yielding the sub-title product (1.35 g, 84%) as a red solid.

¹H-NMR (300 MHz, CDCl₃): δ 1.45 (9H, s), 2.12 (2H, p, J 6.8 Hz), 2.94 (4H, s), 3.18 (2H, t, J 5.6 Hz), 4.26 (2H, t, 7.2 Hz), 7.35–7.42 (3H, m), 8.35–8.44 (2H, m).

b) {3-[3-(3,6-Dioxo-4,6,7,8-tetrahydro-3H-cyclopenta[g]quinoxaln-2-yl)-indol-1-yl]-propyl}-carbamic Acid Tert-butyl Ester The product of step a) (0.44 g, 1.0 mmol) and 5,6-diamino-indan-1-one (0.19 g, 1.17 mmol) was dissolved in THF (10 ml) and the mixture stirred at room temperature for 16 hours. During the course of the reaction a yellow precipitate forms. Diethyl ether (10 ml) was added and the precipitate was removed by filtration, subsequent washing of the solid with THF-diethyl ether and warm methanol furnishes the subtitle product as a yellow solid.

¹H-NMR (300 MHz, DMSO-d6): δ 1.39 (s, 9H), 1.94 (2H, m), 2.70 (2H, m), 2.98 (2H, m), 3.18 (2H, m), 4.35 (2H, m), 7.03–9.07 (8H, m).

The crude product of step b) was dissolved in dichloromethane (3 ml), trifluoroacetic acid (3 ml) and one drop of water. Stirring for five hours followed by evaporation gave the title product as a yellow solid.

¹H-NMR (300 MHz, DMSO-d6): δ 2.13 (2H, p, J 7.4 Hz), 2.73 (2H, t, 6.0 Hz), 2.85 (2H, t, J 8.0 Hz), 3.21 (2H, t, 6.0 Hz), 4.48 (2H, t, J 6.8 Hz), 7.30–7.40 (2H, m), 7.53 (1H, s), 7.69 (1H, d, 7.2 Hz), 7.77 (2H, m), 8.02 (1H, s), 8.97 (1H, d, J7.2 Hz), 9.12 (1H, s), 12.6 (1H, s).

FAB-MS: m/z 373.1 [MH+].

Example 9

3-[1-(3-Amino-propyl)-1H-indol-3-yl]-1-benzyl-1H-benzo[g]quinoxalin-2-one Trifluoroacetic Acid Salt a) {3-[3-(3-Oxo-3,4-dihydro-benzo[g]quinoxalin-2-yl)-indol-1-yl]-propyl}-carbamic Acid tert-Butyl Ester The product of Example 8, step a) (1.60 g, 3.6 mmol) and 2,3-diaminonaphthalene (0.74 g, 4.6 mmol) was dissolved in THF (10 ml) and the mixture stirred at room temperature for 16 hours. During the course of the reaction a yellow precipitate forms. Diethyl ether (10 ml) was added and the precipitate was removed by filtration, subsequent washing of the solid with THF-diethyl ether furnishes the sub-title product (1.35 g, 80%) as a yellow solid.

¹H-NMR (400 MHz, DMSO-d6): δ 1.39 (s, 9H), 1.95 (2H, p, J 6.4 Hz), 3.00 (2H, m), 4.36 (2H, t, J6.8 Hz), 7.02 (1H, m), 7.32 (2H, m), 7.45 (1H, t, J7.2 Hz), 7.51 (1H, t, J7.2 ), 7.63 (1H, m), 7.67 (1H, s), 7.93 (1H, d, J 8.4 Hz), 8.08 (1H, d, J 8.0 Hz), 8.48 (1H, s), 9.01 (2H, m).

b) {3-[3-(4-Benzyl-3-oxo-3,4-dihydro-benzo[g]quinoxalin-2-yl)-indol-1-yl]propyl}-carbamic Acid tert-Butyl Ester The product of step a) (0.24 g, 0.5 mmol) was dissolved in DMF (5 ml) and sodium hydride (0.022 g, 60%, 0.55 mmol) added. After stirring for 30 minutes the solution was cooled to −10° C. and benzyl bromide (0.1 ml, 0.92 mmol) added. After stirring for five hours at room temperature ethyl acetate (10 ml) was added. The organic phase was washed with water (3×25 ml), dried over Na₂SO₄. Removal of the solvent and chromatography yields the subtitle product.

The product of step b) was dissolved in dichloromethane (3 ml) and trifluoroacetic acid (3 ml) and one drop of water. Stirring for five hours followed by evaporation gave the title product as a yellow solid.

¹H-NMR (500 MHz, DMSO-d6): δ 2.12 (2H, p, J 7.5 Hz), 2.83 (2H, m), 4.45 (2H, t, J 6.5 Hz), 5.70 (2H, s), 7.26 (1H, t, J 7.5 Hz), 7.32–7.41 (6H, m), 7.48–7.52 (2H, m), 7.69–7.71 (1H, m), 7.92 (11H, d, J 7.5 Hz), 7.93 (1H, s), 8.10 (1H, d, J 8.0 Hz), 8.57 (1H, s), 9.06–9.04 (2H, m).

The following examples were synthesized following the methods described above:

Example 10

3-[5-(3-Amino-propyl)-5H-[1,3]dioxolo[4,5-f]indol-7-yl]-6,7,8,9-tetrahydro 1H-benzo[g]quinoxalin-2-one Acetic Acid Salt FAB-MS: m/z 417.5 [MH+]

Example 11

3-[1-(3-Amino-propyl)-5-dibenzylamino-1H-indol-3-yl]-6,7,8,9-tetrahydro-1H-benzo[g]quinoxalin-2-one Acetic Acid Salt FAB-MS: m/z 568.7 [MH+]

Example 12

3-[1-(3-Amino-propyl)-2-(4-chloro-phenyl)-1H-indol-3-yl]-6,7,8,9-tetrahydro-1H-benzo[g]quinoxalin-2-one Acetic Acid Salt FAB-MS: m/z 484.0 [MH+]

Example 13

3-[1-(3-Amino-propyl)-2-methyl-1H-indol-3-yl]-6,7,8,9-tetrahydro-1H-benzo[g]quinoxalin-2-one Acetic Acid Salt FAB-MS: m/z 387.5 [MH+]

Example 14

1-(3-Amino-propyl)-3-(3-oxo-3,4,6,7,8,9-hexahydro-benzo[g]quinoxalin-2-yl)-1H-indole-5-carboxylic Acid Methyl Ester Acetic Acid Salt FAB-MS: ml/z 431.5 [MH+]

Example 15

3-[1-(3-Amino-propyl)-6-nitro-1H-indol-3-yl]-6,7,8,9-tetrahydro-1H-benzo[g]quinoxalin-2-one Acetic Acid Salt FAB-MS: m/z 418.5 [MH+]

Example 16

3-[1-(3-Amino-propyl)-5-methoxy-1H-indol-3-yl]-6,7,8,9-tetrahydro-1H-benzo[g]quinoxalin-2-one Acetic Acid Salt FAB-MS: m/z 403.5 [MH+]

Example 17

2-[5-(3-Aminomethyl-benzyl)-5H-[1,3]dioxolo[4,5-f]indol-7-yl]-4H-benzo[f]quinoxalin-3-one Acetic Acid Salt FAB-MS: m/z 475.5 [MH+]

Example 18

2-[5-(3-Amino-propyl)-5H-[1,3]dioxolo[4,5-f]indol-7-yl]-4H-benzo[f]quinoxalin-3-one Acetic Acid Salt FAB-MS: m/z 413.5 [MH+]

Example 19

2-[1-(3-Amino-propyl)-5-dibenzylamino-1H-indol-3-yl]-4H-benzo[f]quinoxalin-3-one Acetic Acid Salt FAB-MS: m/z 564.7 [MH+]

Example 20

2-[1-(3-Amino-propyl)-2-(4-chloro-phenyl)-1H-indol-3-yl]-4H-benzo[f]quinoxalin-3-one Acetic Acid Salt FAB-MS: m/z 480.0 [MH+]

Example 21

2-[1-(3-Amino-propyl)-2-methyl-1H-indol-3-yl]-4H-benzo[f]quinoxalin-3-one Acetic Acid Salt FAB-MS: m/z 383.5 [MH+]

Example 22

1-(3-Amino-propyl)-3-(3-oxo-3,4-dihydro-benzo[f]quinoxalin-2-yl)-1H-indole-5-carboxylic acid methyl ester Acetic Acid Salt FAB-MS: m/z 427.5 [MH+]

Example 23

2-[1-(3-Amino-propyl)-6-nitro-1H-indol-3-yl]-4H-benzo[f]quinoxalin-3-one Acetic Acid Salt FAB-MS: m/z 414.4 [MH+]

Example 24

2-[1-(3-Amino-propyl)-5-methoxy-1H-indol-3-yl]-4H-benzo[f]quinoxalin-3-one Acetic Acid Salt FAB-MS: m/z 399.5 [MH+]

Example 25

7-[5-(3-Aminomethyl-benzyl)-5H-[1,3]dioxolo[4,5-f]indol-7-yl]-1,5-dihydro-imidazo[4,5-g]quinoxalin-6-one Acetic Acid Salt FAB-MS: m/z 465.5 [MH+]

Example 26

7-[5-(3-Aminopropyl)-5H-[1,3]dioxolo[4,5-f]indol-7-yl]-1,5-dihydro-imidazo[4,5-g]quinoxalin-6-one Acetic Acid Salt FAB-MS: m/z 403.4 [MH+]

Example 27

7-[1-(3-Amino-propyl)-5-dibenzylamino-1H-indol-3-yl]-1,5-dihydro-imidazo[4,5-g]quinoxalin-6-one Acetic Acid Salt FAB-MS: m/z 554.7 [MH+]

Example 28

7-[1-(3-Amino-propyl)-2-(4chloro-phenyl)-1H-indol-3-yl]-1,5-dihydro-imidazo[4,5-g]quinoxalin-6-one Acetic Acid Salt FAB-MS: m/z 469.9 [MH+]

Example 29

7-[1-(3-Amino-propyl)-2-methyl-1H-indol-3-yl]-1,5-dihydro-imidazo[4,5-g]quinoxalin-6-one Acetic Acid Salt FAB-MS: m/z 373.4 [MH+]

Example 30

1-(3-Amino-propyl)-3-(7-oxo-7,8-dihydro-3H-imidazo[4,5-g]quinoxalin-6-yl)-1H-indole-5-carboxylic acid methyl ester Acetic Acid Salt FAB-MS: m/z 417.4 [MH+]

Example 31

7-[1-(3-Amino-propyl)-6-nitro-1H-indol-3-yl]-1,5-dihydro-imidazo[4,5-g]quinoxalin-6-one Acetic Acid Salt FAB-MS: m/z 404.4 [MH+]

Example 32

7-[1-(3-Amino-propyl)-5-methoxy-1H-indol-3-yl]-1,5-dihydro-imidazo[4,5-g]quinoxalin-6-one Acetic Acid Salt FAB-MS: m/z 389.4 [MH+]

Example 33

7-[5-(3-Aminomethyl-benzyl)-5H-[1,3]dioxolo[4,5-f]indol-7-yl]-2,3-dihydro-5H-1,4-dioxa-5,8-diaza-anthracen-6-one Acetic Acid Salt FAB-MS: m/z 483.5 [MH+]

Example 34

7-[5-(3-Amino-propyl)-5H-[1,3]dioxolo[4,5-f]indol-7-yl]-2,3-dihydro-5H-1,4-dioxa-5,8-diaza-anthracen-6-one Acetic Acid Salt FAB-MS: m/z 421.4 [MH+]

Example 35

7-[1-(3-Amino-propyl)-5-dibenzylamino-1H-indol-3-yl]-2,3-dihydro-5H-1,4-dioxa-5,8-diaza-anthracen-6-one Acetic Acid Salt FAB-MS: m/z 572.7 [MH+]

Example 36

7-[1-(3-Amino-propyl)-2-(4chloro-phenyl)-1H-indol-3-yl]-2,3-dihydro-5H-1,4-dioxa-5,8-diaza-anthracen-6-one Acetic Acid Salt FAB-MS: m/z 488.0 [MH+]

Example 37

7-[1-(3-Amino-propyl)-2-methyl-1H-indol-3-yl]-2,3-dihydro-5H-1,4-dioxa-5,8-diaza-anthracen-6-one Acetic Acid Salt FAB-MS: m/z 391.4 [MH+]

Example 38

1-(3-Amino-propyl)-3-(7-oxo-2,3,7,8-tetrahydro-1,4-dioxa-5,8-diaza-anthracen-6-yl)-1H-indole-5-carboxylic Acid Methyl Ester Acetic Acid Salt FAB-MS: m/z 435.5 [MH+]

Example 39

7-[1-(3-Amino-propyl)-6-nitro-1H-indol-3-yl]-2,3-dihydro-5H-1,4-dioxa-5,8-diaza-anthracen-6-one Acetic Acid Salt FAB-MS: m/z 422.4 [MH+]

Example 40

7-[1-(3-Amino-propyl)-5-methoxy-1H-indol-3-yl]-2,3-dihydro-5H-1,4-dioxa-5,8-diaza-anthracen-6-one Acetic Acid Salt FAB-MS: m/z 407.4 [MH+]

Example 41

7-[5-(3-Aminomethyl-benzyl)-5H-[1,3]dioxolo[4,5-f]indol-7-yl]-1,5-dihydro-1,2,5,8-tetraaza-cyclopenta[b]naphthalen-6-one Acetic Acid Salt FAB-MS: m/z 465.5 [MH+]

Example 42

7-[5-(3-Amino-propyl)-5H-[1,3]dioxolo[4,5-f]indol-7-yl]-1,5-dihydro-1,2,5,8-tetraaza-cyclopenta[b]naphthalen-6-one Acetic Acid Salt FAB-MS: m/z 403.4 [NH+]

Example 43

7-[1-(3-Amino-propyl)-5-dibenzylamino-1H-indol-3-yl]-1,5-dihydro-1,2,5,8-tetraaza-cyclopenta[b]naphthalen-6-one Acetic Acid Salt FAB-MS: m/z 554.7 [MH+]

Example 44

7-[1-(3-Amino-propyl)-2-methyl-1H-indol-3-yl]-1,5-dihydro-1,2,5,8-tetraaza-cyclopenta[b]naphthalen-6-one Acetic Acid Salt FAB-MS: m/z 373.4 [MH+]

Example 45

1-(3-Amino-propyl)-3-(6-oxo-5,6-dihydro-1H-1,2,5,8-tetraaza-cyclopenta[b]naphthalen-7-yl)-1H-indole-5-carboxylic Acid Methyl Ester Acetic Acid Salt FAB-MS: m/z 417.4 [MH+]

Example 46

7-[1-(3-Amino-propyl)-6-nitro-1H-indol-3-yl]-1,5-dihydro-1,2,5,8-tetraaza-cyclopenta[b]naphthalen-6-one Acetic Acid Salt FAB-MS: m/z 404.4 [MH+]

Example 47

7-[1-(3-Amino-propyl)-5-methoxy-1H-indol-3-yl]-1,5-dihydro-1,2,5,8-tetraaza-cyclopenta[b]naphthalen-6-one Acetic Acid Salt FAB-MS: m/z 389.4 [MH+]

Example 48

7-[5-(3-Aminomethyl-benzyl)-5H-[1,3]dioxolo[4,5-f]indol-7-yl]-2-hydroxy-1,5-dihydro-imidazo[4,5-g]quinoxalin-6-one Acetic Acid Salt FAB-MS: m/z 481.5 [MH+]

Example 49

7-[5-(3-Amino-propyl)-5H-[1,3]dioxolo[4,5-f]indol-7-yl]-2-hydroxy-1,5-dihydro-imidazo[4,5-g]quinoxalin-6-one Acetic Acid Salt FAB-MS: m/z 419.4 [MH+]

Example 50

7-[1-(3-Amino-propyl)-5-dibenzylamino-1H-indol-3-yl]-2-hydroxy-1,5-dihydro-imidazo[4,5-g]quinoxalin-6-one Acetic Acid Salt FAB-MS: m/z 570.7 [MH+]

Example 51

7-[1-(3-Amino-propyl)-2-(4-chloro-phenyl)-1H-indol-3-yl]-2-hydroxy-1,5-dihydro-imidazo[4,5-g]quinoxalin-6-one Acetic Acid Salt FAB-MS: m/z 485.9 [MH+]

Example 52

7-[1-(3-Amino-propyl)-2-methyl-1H-indol-3-yl]-2-hydroxy-1,5-dihydro-imidazo[4,5-g]quinoxalin-6-one Acetic Acid Salt FAB-MS: m/z 389.4 [MH+]

Example 53

1-(3-Amino-propyl)-3-(2-hydroxy-7-oxo-7,8-dihydro-3H-imidazo[4,5-g]quinoxalin-6-yl)-1H-indole-5-carboxylic Acid Methyl Ester Acetic Acid Salt FAB-MS: m/z 433.4 [MH+]

Example 54

7-[1-(3-Amino-propyl)-6-nitro-1H-indol-3-yl]-2-hydroxy-1,5-dihydro-imidazo[4,5-g]quinoxalin-6-one Acetic Acid Salt FAB-MS: m/z 420.4 [MH+]

Example 55

7-[1-(3-Amino-propyl)-5-methoxy-1H-indol-3-yl]-2-hydroxy-1,5-dihydro-imidazo[4,5-g]quinoxalin-6-one Acetic Acid Salt FAB-MS: m/z 405.4 [MH+]

Example 56

3-[1-(3-Amino-propyl)-5-dibenzylamino-1H-indol-3-yl]-1H-pyrazino[2,3-g]quinoxalin-2-one Acetic Acid Salt FAB-MS: m/z 566.7 [MH+]

Example 57

3-[5-(3-Aminomethyl-benzyl)-5H-[1,3]dioxolo[4,5-f]indol-7-yl]-7,8-dimethyl-1H-pyrazino[2,3-g]quinoxalin-2-one Acetic Acid Salt FAB-MS: m/z 505.6 [MH+]

Example 58

3-[1-(3-Amino-propyl)-5-dibenzylamino-1H-indol-3-yl]-7,8-dimethyl-1H-pyrazino[2,3-g]quinoxalin-2-one Acetic Acid Salt FAB-MS: m/z 594.7 [MH+]

Example 59

3-[1-(3-Amino-propyl)-5-methoxy-1H-indol-3-yl]-7,8-dimethyl-1H-pyrazino[2,3-g]quinoxalin-2-one Acetic Acid Salt FAB-MS: m/z 429.5 [MH+]

Example 60

3-[1-(3-Amino-propyl)-6-benzyloxy-1H-indol-3-yl]-6,7,8,9-tetrahydro-1H-benzo[g]quinoxalin-2-one Acetic Acid Salt FAB-MS: m/z 479.6 [MH+]

Example 61

3-[1-(3-Amino-propyl)-5-benzyloxy-1H-indol-3-yl]-6,7,8,9-tetrahydro-1H-benzo[g]quinoxalin-2-one Acetic Acid Salt FAB-MS: m/z 479.6 [MH+]

Example 62

3-[1-(3-Amino-propyl)-5-bromo-1H-indol-3-yl]-6,7,8,9-tetrahydro-1H-benzo[g]quinoxalin-2-one Acetic Acid Salt FAB-MS: m/z 451.1, 453.1 [MH+]

Example 63

3-[1-(3-Amino-propyl)-2-ethyl-1H-indol-3-yl]-6,7,8,9-tetrahydro-1H-benzo[g]quinoxalin-2-one Acetic Acid Salt FAB-MS: m/z 401.5 [MH+]

Example 64

3-[1-(4-Amino-butyl)-2-benzyl-1H-indol-3-yl]-6,7,8,9-tetrahydro-1H-benzo[g]quinoxalin-2-one Acetic Acid Salt FAB-MS: m/z 477.6 [MH+]

Example 65

3-[1-(6-Aminomethyl-pyridin-2-ylmethyl)-1H-indol-3-yl]-6,7,8,9-tetrahydro-1H-benzo[g]quinoxalin-2-one Acetic Acid Salt FAB-MS: m/z 436.5 [MH+]

Example 66

3-[1-(4-Aminomethyl-benzyl)-1H-indol-3-yl]-6,7,8,9-tetrahydro-1H-benzo[g]quinoxalin-2-one Acetic Acid Salt FAB-MS: m/z 435.5 [MH+]

Example 67

3-[1-(3-Aminomethyl-benzyl)-1H-indol-3-yl]-6,7,8,9-tetrahydro-1H-benzo[g]quinoxalin-2-one Acetic Acid Salt FAB-MS: m/z 435.5 [MH+]

Example 68

3-[1-(4-Amino-butyl)-1H-indol-3-yl]-6,7,8,9-tetrahydro-1H-benzo[g]quinoxalin-2-one Acetic Acid Salt FAB-MS: m/z 387.5 [MH+]

Example 69

3-[1-(3-Amino-propyl)-1H-indol-3-yl]-6,7,8,9-tetrahydro-1H-benzo[g]quinoxalin-2-one Acetic Acid Salt FAB-MS: m/z 373.5 [MH+]

Example 70

2-[1-(3-Amino-propyl)-6-benzyloxy-1H-indol-3-yl]-4H-benzo[f]quinoxalin-3-one Acetic Acid Salt FAB-MS: m/z 475.6 [MH+]

Example 71

2-[1-(3-Amino-propyl)-5-benzyloxy-1H-indol-3-yl]-4H-benzo[f]quinoxalin-3-one Acetic Acid Salt FAB-MS: m/z 475.6 [MH+]

Example 72

2-[1-(3-Amino-propyl)-5-bromo-1H-indol-3-yl]-4H-benzo[f]quinoxalin-3-one Acetic Acid Salt FAB-MS: m/z 447.0, 449.0 [MH+]

Example 73

2-[1-(3-Amino-propyl)-2-ethyl-1H-indol-3-yl]-4H-benzo[f]quinoxalin-3-one Acetic Acid Salt FAB-MS: m/z 397.5 [MH+]

Example 74

2-[1-(4-Amino-butyl)-2-benzyl-1H-indol-3-yl]-4H-benzo[f]quinoxalin-3-one Acetic Acid Salt FAB-MS: m/z 473.6 [MH+]

Example 75

2-[1-(6-Aminomethyl-pyridin-2-ylmethyl)-1H-indol-3-yl]-4H-benzo[f]quinoxalin-3-one Acetic Acid Salt FAB-MS: m/z 432.5 [MH+]

Example 76

2-[1-(4-Aminomethyl-benzyl)-1H-indol-3-yl]-4H-benzo[f]quinoxalin-3-one Acetic Acid Salt FAB-MS: m/z 431.5 [MH+]

Example 77

2-[1-(3-Aminomethyl-benzyl)-1H-indol-3-yl]-4H-benzo[f]quinoxalin-3-one Acetic Acid Salt FAB-MS: m/z 431.5 [MH+]

Example 78

2-[1-(4-Amino-butyl)-1H-indol-3-yl]-4H-benzo[f]quinoxalin-3-one Acetic Acid Salt FAB-MS: m/z 383.5 [MH+]

Example 79

2-[1-(3-Amino-propyl)-1H-indol-3-yl]-4H-benzo[f]quinoxalin-3-one Acetic Acid Salt FAB-MS: m/z 369.4 [MH+]

Example 80

7-[1-(3-Amino-propyl)-6-benzyloxy-1H-indol-3-yl]-1,5-dihydro-imidazo[4,5-g]quinoxalin-6-one Acetic Acid Salt FAB-MS: m/z 465.5 [MH+]

Example 81

7-[1-(3-Amino-propyl)-5-benzyloxy-1H-indol-3-yl]-1,5-dihydro-imidazo[4,5-g]quinoxalin-6-one Acetic Acid Salt FAB-MS: m/z 465.5 [MH+]

Example 82

7-[1-(3-Amino-propyl)-5-bromo-1H-indol-3-yl]-1,5-dihydro-imidazo[4,5-g]quinoxalin-6-one Acetic Acid Salt FAB-MS: m/z 437.00, 439.0 [MH+]

Example 83

7-[1-(3-Amino-propyl)-2-ethyl-1H-indol-3-yl]-1,5-dihydro-imidazo[4,5-g]quinoxalin-6-one Acetic Acid Salt FAB-MS: m/z 387.5 [MH+]

Example 84

7-[1-(4-Amino-butyl)-2-benzyl-1H-indol-3-yl]-1,5-dihydro-imidazo[4,5-g]quinoxalin-6-one Acetic Acid Salt FAB-MS: m/z 463.6 [MH+]

Example 85

7-[1-(6-Aminomethyl-pyridin-2-ylmethyl)-1H-indol-3-yl]-1,5-dihydro-imidazo[4,5-g]quinoxalin-6-one Acetic Acid Salt FAB-MS: m/z 422.5 [MH+]

Example 86

7-[1-(4-Aminomethyl-benzyl)-1H-indol-3-yl]-1,5-dihydro-imidazo[4,5-g]quinoxalin-6-one Acetic Acid Salt FAB-MS: m/z 421.5 [MH+]

Example 87

7-[1-(3-Aminomethyl-benzyl)-1H-indol-3-yl]-1,5-dihydro-imidazo[4,5-g]quinoxalin-6-one Acetic Acid Salt FAB-MS: m/z 421.5 [MH+]

Example 88

7-[1-(4-Amino-butyl)-1H-indol-3-yl]-1,5-dihydro-imidazo[4,5-g]quinoxalin-6-one Acetic Acid Salt FAB-MS: m/z 373.4 [MH+]

Example 89

7-[1-(3-Amino-propyl)-1H-indol-3-yl]-1,5-dihydro-imidazo[4,5-g]quinoxalin-6-one Acetic Acid Salt FAB-MS: m/z 359.4 [MH+]

Example 90

7-[1-(3-Amino-propyl)-6-benzyloxy-1H-indol-3-yl]-2,3-dihydro-5H-1,4-dioxa-5,8-anthracen-6-one Acetic Acid Salt FAB-MS: m/z 483.5 [MH+]

Example 91

7-[1-(3-Amino-propyl)-5-benzyloxy-1H-indol-3-yl]-2,3-dihydro-5H-1,4-dioxa-5,8-diaza-anthracen-6-one Acetic Acid Salt FAB-MS: m/z 483.5 [MH+]

Example 92

7-[1-(3-Amino-propyl)-5-bromo-1H-indol-3-yl]-2,3-dihydro-5H-1,4-dioxa-5,8-diaza-anthracen-6-one Acetic Acid Salt FAB-MS: m/z 455.0, 457.0 [MH+]

Example 93

7-[1-(3-Amino-propyl)-2-ethyl-1H-indol-3-yl]-2,3-dihydro-5H-1,4-dioxa-5,8-diaza-anthracen-6-one acetic acid salt FAB-MS: m/z 405.5 [MH+]

Example 94

7-[1-(4-Amino-butyl)-2-benzyl-1H-indol-3-yl]-2,3-dihydro-5H-1,4-dioxa-5,8-diaza-anthracen-6-one acetic acid salt FAB-MS: m/z 481.6 [MH+]

Example 95

7-[1-(6-Aminomethyl-pyridin-2-ylmethyl)-1H-indol-3-yl]-2,3-dihydro-5H-1,4-dioxa-5,8-diaza-anthracen-6-one acetic acid salt FAB-MS: m/z 440.5 [MH+]

Example 96

7-[1-(4-Aminomethyl-benzyl)-1H-indol-3-yl]-2,3-dihydro-5H-1,4-dioxa-5,8-diaza-anthracen-6-one acetic acid salt FAB-MS: m/z 439.5 [MH+]

Example 97

7-[1-(3-Aminomethyl-benzyl)-1H-indol-3-yl]-2,3-dihydro-5H-1,4-dioxa-5,8-diaza-anthracen-6-one acetic acid salt FAB-MS: m/z 439.5 [MH+]

Example 98

7-[1-(4-Amino-butyl)-1H-indol-3-yl]-2,3-dihydro-5H-1,4-dioxa-5,8-diaza-anthracen-acetic acid salt FAB-MS: m/z 391.4 [MH+]

Example 99

7-[1-(3-Amino-propyl)-1H-indol-3-yl]-2,3-dihydro-5H-1,4-dioxa-5,8-diaza-anthracen-6-one acetic acid salt FAB-MS: m/z 377.4 [MH+]

Example 100

7-[1-(3-Amino-propyl)-6-benzyloxy-1H-indol-3-yl]-1,5-dihydro-1,2,5,8-tetraaza-cyclopenta[b]naphthalen-6-one acetic acid salt FAB-MS: m/z 465.5 [MH+]

Example 101

7-[1-(3-Amino-propyl)-5-benzyloxy-1H-indol-3-yl]-1,5-dihydro-1,2,5,8-tetraaza-cyclopenta[b]naphthalen-6-one acetic acid salt FAB-MS: m/z 465.5 [MH+]

Example 102

7-[1-(3-Amino-propyl)-5-bromo-1H-indol-3-yl]-1,5-dihydro-1,2,5,8-tetraaza-cyclopenta[b]naphthalen-6-one acetic acid salt FAB-MS: m/z 437.0, 439.0 [MH+]

Example 103

7-[1-(3-Amino-propyl)-2-ethyl-1H-indol-3-yl]-1,5-dihydro-1,2,5,8-tetraaza-cyclopenta[b]naphthalen-6-one acetic acid salt FAB-MS: m/z 387.5 [MH+]

Example 104

7-[1-(4-Amino-butyl)-2-benzyl-1H-indol-3-yl]-1,5-dihydro-1,2,5,8-tetraaza-cyclopenta[b]naphthalen-6-one acetic acid salt FAB-MS: m/z 463.6 [MH+]

Example 105

7-[1-(6-Aminomethyl-pyridin-2-ylmethyl)-1H-indol-3-yl]-1,5-dihydro-1,2,5,8-tetraaza-cyclopenta[b]naphthalen-6-one acetic acid salt FAB-MS: m/z 422.5 [MH+]

Example 106

7-[1-(4-Aminomethyl-benzyl)-1H-indol-3-yl]-1,5-dihydro-1,2,5,8-tetraaza-cyclopenta[b]naphthalen-6-one acetic acid salt FAB-MS: m/z 421.5 [MH+]

Example 107

7-[1-(3-Aminomethyl-benzyl)-1H-indol-3-yl]-1,5-dihydro-1,2,5,8-tetraaza-cyclopenta[b]naphthalen-6-one acetic acid salt FAB-MS: m/z 421.5 [MH+]

Example 108

7-[(1-(Amino-butyl)-1H-indol-3-yl]-1,5-dihydro-1,2,5,8-tetraaza-cyclopenta[b]naphthalen-6-one acetic acid salt FAB-MS: m/z 373.4 [MH+]

Example 109

7-[1-(3-Amino-propyl)-1H-indol-3-yl]-1,5-dihydro-1,2,5,8-tetraaza-cyclopenta[b]naphthalen-6-one acetic acid salt FAB-MS: m/z 359.4 [MH+]

Example 110

7-[1-(3-Amino-propyl)-6-benzyloxy-1H-indol-3-yl]-2-hydroxy-1,5hydro-imidazo[4,5g]quinoxalin-6-one acetic acid salt FAB-MS: m/z 481.5 [MH+]

Example 111

7-[1-(3-Amino-propyl)-5-benzyloxy-1H-indol-3-yl]-2-hydroxy-1,5-dihydro-imidazo[4,5-g]quinoxalin-6-one acetic acid salt FAB-MS: m/z 481.5 [MH+]

Example 112

7-[1-(3-Amino-propyl)-5-bromo-1H-indol-3-yl]-2-hydroxy-1,5-dihydro-imidazo[4,5-g]quinoxalin-6-one acetic acid salt FAB-MS: m/z 453.0,455.0 [MH+]

Example 113

7-[1-(3-Amino-propyl)-2-ethyl-1H-indol-3-yl]-2-hydroxy-1,5-dihydro-imidazo[4,5-g]quinoxalin-6-one acetic acid salt FAB-MS: m/z 403.5 [MH+]

Example 114

7-[1-(4-Amino-butyl)-2-benzyl-1H-indol-3-yl]-2-hydroxy-1,5-dihydro-imidazo[4,5-g]quinoxalin-6-one acetic acid salt FAB-MS: m/z 479.6 [MH+]

Example 115

7-[1-(6-Aminomethyl-pyridin-2-ylmethyl)-1-H-indol-3-yl]-2-hydroxy-1,5-dihydro-imidazo[4,5-g]quinoxalin-6-one acetic acid salt FAB-MS: m/z 438.5 [MH+]

Example 116

7-[1-(4-Aminomethyl-benzyl)-1H-indol-3-yl]-2-hydroxy-1,5-dihydro-imidazo[4,5-g]quinoxalin-6-one acetic acid salt FAB-MS: m/z 437.5 [H+]

Example 117

7-[1-(3-Aminomethyl-benzyl)-1H-indol-3-yl]-2-hydroxy-1,5-dihydro-imidazo[4,5-g]quinoxalin-6-one acetic acid salt FAB-MS: m/z 437.5 [MH+]

Example 118

7-[1-(4-Amino-butyl)-1H-indol-3-yl]-2-hydroxy-1,5-dihydro-imidazo[4,5-g]quinoxalin-6-one acetic acid salt FAB-MS: m/z 389.4 [MH+]

Example 119

7-(1-(3-Aminopropyl)-1H-indol-3-yl]-2-hydroxy-1,5-dihydro-imidazo[4,5-g]quinoxalin-6-one acetic acid salt FAB-MS: m/z 375.4 [MH+]

Example 120

3-[1-(4-Aminomethyl-benzyl)-1H-indol-3-yl]-1H-pyrazino[2,3-g]quinoxalin-2-one acetic acid salt FAB-MS: m/z 433.5 [MH+]

Example 121

3-[1-(3-Aminomethyl-benzyl)-1H-indol-3-yl]-1H-pyrazino[2,3-g]quinoxalin-2-one acetic acid salt FAB-MS: m/z 433.5 [MH+]

Example 122

3-[1-(4-Amino-butyl)-1H-indol-3-yl]-1H-pyrazino[2,3-g]quinoxalin-2-one acetic acid salt FAB-MS: m/z 385.4 [MH+]

Example 123

3-[1-(3-Amino-propyl)-6-benzyloxy-1H-indol-3-yl)-7,8-dimethyl-1H-pyrazino[2,3-g]quinoxalin-2-one acetic acid salt FAB-MS: m/z 505.6 [MH+]

Example 124

3-[1-(3-Aminopropyl)-5-benzyloxy-1H-indol-3-yl]-7,8-dimethyl-1H-pyrazino[2,3-g]quinoxalin-2-one acetic acid salt FAB-MS: m/z 505.6 [MH+]

Example 125

3-[1-(3-Amino-propyl)-5-bromo-1H-indol-3-yl]-7,8-dimethyl-1H-pyrazino(2,3-g]quinoxalin-2-one acetic acid salt FAB-MS: m/z 477.0,479.0 [MH+]

Example 126

3-(1-(4-Aminomethyl-benzyl)-1H-indol-3-yl]-7,8-dimethyl-1H-pyrazino[2,3-g]quinoxalin-2-one acetic acid salt FAB-MS: m/z 461.5 [MH+]

Example 127

3-[1-(3-Aminomethyl-benzyl)-1H-indol-3-yl]-7,8-dimethyl-1H-pyrazino[2,3-g]quinoxalin-2-one acetic acid salt FAB-MS: m/z 461.5 [MH+]

Example 128

3-[1-(4-Amino-butyl)-1H-indol-3-yl]-7,8-dimethyl-1H-pyrazino[2,3-g]quinoxalin-2-one acetic acid salt FAB-MS: m/z 413.5 [MH+]

Example 129

3-[1-(3-Amino-propyl)-1H-indol-3-yl]-7,8-dimethyl-1H-pyrazino[2,3-g]quinoxalin-2-one acetic acid salt FAB-MS: m/z 399.5 [MH+]

Example 130

3-[5-(3-Aminomethyl-benzyl)-5H-[1,3]dioxolo[4,5-f]indol-7-yl]-1,6,7,8-tetrahydro-cyclopenta[g]quinoxalin-2-one acetic acid salt FAB-MS: m/z 465.5 [MH+]

Example 131

3-[5-(3-Amino-propyl)-5H-[1,3]dioxolo[4,5-f]indol-7-yl]-1,6,7,8-tetrahydro-cyclopenta[g]quinoxalin-2-one acetic acid salt FAB-MS: m/z 403.5 [MH+]

Example 132

3-[1-(3-Amino-propyl)-5-dibenzylamino-1H-indol-3-yl]-1,6,7,8-tetrahydro-cyclopenta[g]quinoxalin-2-one acetic acid salt FAB-MS: m/z 554.7 [MH+]

Example 133

3-[1-(3-Amino-propyl)-2-(4-chloro-phenyl)-1H-indol-3-yl]-1,6,7,8-tetrahydro-cyclopenta[g]quinoxalin-2-one acetic acid salt FAB-MS: n/z 470.0 [MH+]

Example 134

3-[1-(3-Amino-propyl)-2-methyl-1H-indol-3-yl]-1,6,7,8-tetrahydro-cyclopenta[g]quinoxalin-2-one acetic acid salt FAB-MS: m/z 373.5 [MH+]

Example 135

1-(3-Amino-propyl)-3-(3-oxo-4,6,7,8-tetrahydro-3H-cyclopenta[g]quinoxalin-2-yl)-1H-indole-5-carboxylic acid methyl ester acetic acid salt FAB-MS: m/z 417.5 [MH+]

Example 136

3-[1-(3-Amino-propyl)-6-nitro-1H-indol-3-yl]-1,6,7,8-tetrahydro-cyclopenta[g]quinoxalin-2-one acetic acid salt FAB-MS: m/z 404.4 [MH+]

Example 137

3-[1-(3-Amino-propyl)-5-methoxy-1H-indol-3-yl]-1,6,7,8-tetrahydro-cyclopenta[g]quinoxalin-2-one acetic acid salt FAB-MS: m/z 389.5 [MH+]

Example 138

7-[5-(3-Aminomethyl-benzyl)-5H-[1,3]dioxolo[4,5-f]indol-7-yl]-5H-1,3-dioxa-5,8-diaza-cyclopenta[b]naphthalen-6-one acetic acid salt FAB-MS: m/z 469.5 [MH+]

Example 139

7-[5-(3-Amino-propyl)-5H-[1,3]dioxolo[4,5-f]indol-7-yl]-5H-1,3-dioxa-5,8-diaza-cyclopenta[b]naphthalen-6-one acetic acid salt FAB-MS: m/z 407.4 [MH+]

Example 140

7-[1-(3-Amino-propyl)-2-(4-chloro-phenyl)-1H-indol-3-yl]-5H-1,3-dioxa-5,8-diaza-cyclopenta[b]naphthalen-6-one acetic acid salt FAB-MS: m/z 473.9 [MH+]

Example 141

7-[1-(3-Amino-propyl)-2-methyl-1H-indol-3-yl]-5H-1,3-dioxa-5,8-diaza-cyclopenta[b]naphthalen-6-one acetic acid salt FAB-MS: m/z 377.4 [MH+]

Example 142

1-(3-Amino-propyl)-3-(7-oxo-7,8-dihydro-1,3-dioxa-5,8-diaza-cyclopenta[b]naphthalen-6-yl)-1H-indole-5-carboxylic acid methyl ester acetic acid salt FAB-MS: m/z 421.4 [MH+]

Example 143

7-[1-(3-Amino-propyl)-6-nitro-1H-indol-3-yl]-5H-1,3-dioxa-5,8-diaza-cyclopenta[b]naphthalen-6-one acetic acid salt FAB-MS: m/z 408.4 [MH+]

Example 144

7-[1-(3-Amino-propyl)-5-methoxy-1H-indol-3-yl]-5H-1,3-dioxa-5,8-diaza-cyclopenta[b]naphthalen-6-one acetic acid salt FAB-MS: m/z 393.4 [MH+]

Example 145

6-[5-3-Aminomethyl-benzyl)-5H-[1,3]dioxolo[4,5-f]indol-7-yl]-2,3-dihydro-8H-1,4-dioxa-5,8-diaza-phenanthren-7-one acetic acid salt FAB-MS: m/z 483.5 [MH+]

Example 146

6-[5-(3-Amino-propyl)-5H-[1,3]dioxolo[4,5-f]indol-7-yl]-2,3-dihydro-8H-1,4-diaza-phenanthren-7-one acetic acid salt FAB-MS: m/z 421.4 [MH+]

Example 147

6-[1-(3-Amino-propyl)-5-dibenzylamino-1H-indol-3-yl]-2,3-dihydro-8H-1,4-dioxa-5,8-diaza-phenanthren-7-one acetic acid salt FAB-MS: m/z 572.7 [MH+]

Example 148

6-[1-(3-Amino-propyl)-2-(4-chloro-phenyl)-1H-indol-3-yl]-2,3-dihydro-8H-1,4-dioxa-5,8-diaza-phenanthren-7-one acetic acid salt FAB-MS: m/z 488.0 [MH+]

Example 149

6-[1-(3-Amino-propyl)-2-methyl-1H-indol-3-yl]-2,3-dihydro-8H-1,4-dioxa-5,8-diaza-phenanthren-7-one acetic acid salt FAB-MS: m/z 391.4 [MH+]

Example 150

1-(3-Amino-propyl)-3-(7-oxo-2,3,7,8-tetrahydro-1,4-dioxa-5,8-diaza-phenanthren-6-yl)-1H-indole-5-carboxylic acid methyl ester acetic acid salt FAB-MS: m/z 435.5 [MH+]

Example 151

6-[1-(3-Amino-propyl)-6-nitro-1H-indol-3-yl]-2,3-dihydro-8H-1,4-dioxa-5,8-diaza-phenanthren-7-one acetic acid salt FAB-MS: m/z 422.4 [MH+]

Example 152

6-[1-(3-Amino-propyl)-5-methoxy-1H-indol-3-yl]-2,
3-dihydro-8H-1,4-dioxa-5,8-diaza-phenanthren-7-
one acetic acid salt FAB-MS: m/z 407.4 [MH+]

Example 153

6-Acetyl-2-[5-(3-aminomethyl-benzyl)-5H-[1,3]
dioxolo[4,5-f]indol-7-yl]-4,6,7,8-tetrahydro-pyrrolo
[2,3-g]quinoxalin-3-one acetic acid salt FAB-MS: m/z 508.6 [MH+]

Example 154

6-Acetyl-2-[5-(3-amino-propyl)-5H-[1,3]dioxolo[4,
5-f]indol-7-yl]-4,6,7,8-tetrashrdro-pyrrolo[2,3-g]
quinoxalin-3-one acetic acid salt FAB-MS: m/z 446.5 [MH+]

Example 155

6-Acetyl-2-[1-(3-amino-propyl)-5-dibenzylamino-
1H-indol-3-yl]-4,6,7,8-tetrahydro-pyrrolo[2,3-g]
quinoxalin-3-one acetic acid salt FAB-MS: m/z 597.7 [MH+]

Example 156

6-Acetyl-2-[1-(3-amino-propyl)-2-(4-chloro-
phenyl)-1H-indol-3-yl)4,6,7,8-tetrahydro-pyrrolo[2,
3-g]quinoxalin-3-one acetic acid salt FAB-MS: m/z 513.0 [MH+]

Example 157

6-Acetyl-2-[1-(3-amino-propyl)-2-methyl-1H-indol-
3-yl]-4,6,7,8-tetrahydro-pyrrolo[2,3-g]quinoxalin-3-
one acetic acid salt FAB-MS: m/z 416.5 [MH+]

Example 158

3-(6-Acetyl-3-oxo-4,6,7,8-tetrahydro-3H-pyrrolo[2,
3-g]quinoxalin-2-yl)-1-(3-amino-propyl)-1H-indole-
5-carboxylic acid methyl ester acetic acid salt FAB-MS: m/z 460.5 [MH+]

Example 159

6-Acetyl-2-(1-(3-amino-propyl)-6-nitro-1H-indol-3-
yl]-4,6,7,8-tetrahydro-pyrrolo[2,3-g]quinoxalin-3-
one acetic acid salt FAB-MS: m/z 447.5 [MH+]

Example 160

6-Acetyl-2-[1-(3-amino-propyl)-5-methoxy-1H-
indol-3-yl]-4,6,7,8-tetrahydro-pyrrolo[2,3g]
quinoxalin-3-one acetic acid salt FAB-MS: m/z 432.5 [MH+]

Example 161

3-[1-(3-Amino-propyl)-6-benzyloxy-1H-indol-3-yl]-
1,6,7,8-tetrahydro-cyclopenta[g]quinoxalin-2-one
acetic acid salt FAB-MS: m/z 465.6 [MH+]

Example 162

3-[1-(3-Amino-propyl)-5-benzyloxy-1H-indol-3-yl]-
1,6,7,8-tetrahydro-cyclopenta[g]quinoxalin-2-one
acetic acid salt FAB-MS: m/z 465.6 [MH+]

Example 163

3-[1-(3-Amino-propyl)-5-bromo-1H-indol-3-yl]-1,6,
7,8-tetrahydro-cyclopenta[g]quinoxalin-2-one acetic
acid salt FAB-MS: m/z 437.0,439.0 [MH+]

Example 164

3-[1-(3-Amino-propyl)-2-ethyl-1H-indol-3-yl]-1,6,7,
8-tetrahydro-cyclopenta[g]quinoxalin-2-one acetic
acid salt FAB-MS: m/z 387.5 [MH+]

Example 165

3-[1-(4-Amino-butyl)-2-benzyl-1H-indol-3-yl]-1,6,7,
8-tetrahydro-cyclopenta[g]quinoxalin-2-one acetic
acid salt FAB-MS: m/z 463.6 [MH+]

Example 166

3-[1-(6-Aminomethyl-pyridin-2-ylmethyl)-1H-indol-
3-yl]-1,6,7,8-tetrahydro-cyclopenta[g]quinoxalin-2-
one acetic acid salt FAB-MS: m/z 422.5 [MH+]

Example 167

3-[1-(4Aminomethyl-benzyl)-1H-indol-3-yl]-1,6,7,
8-tetrahydro-cyclopenta[g]quinoxalin-2-one acetic
acid salt FAB-MS: m/z 421.5 [MH+]

Example 168

3-[1-(3-Aminomethyl-benzyl)-1H-indol-3-yl]-1,6,7,
8-tetrahydro-cyclopenta[g]quinoxalin-2-one acetic
acid salt FAB-MS: m/z 421.5 [MH+]

Example 169

3-[1-(4-Amino-butyl)-1H-indol-3-yl]-1,6,7,8-
tetrahydro-cyclopenta[g]quinoxalin-2-one acetic
acid salt FAB-MS: m/z 373.5 [a+]

Example 170

3-[1-(3-Amino-propyl)-1H-indol-3-yl]-1,6,7,8-
tetrahydro-cyclopenta[g]quinoxalin-2-one acetic
acid salt FAB-MS: m/z 359.4 [MH+]

Example 171

7-[1-(3-Amino-propyl)-6-benzyloxy-1H-indol-3-yl]-
5H-1,3-dioxa-5,8-diaza-cyclopenta[b]naphthalen-6-
one acetic acid salt FAB-MS: m/z 469.5 [MH+]

Example 172

7-[1-(3-Amino-propyl)-5-benzyloxy-1H-indol-3-yl]-5H-1,3-dioxa-5,8-diaza-cyclopenta[b]naphthalen-6one acetic acid salt FAB-MS: m/z 469.5 [MH+]

Example 173

7-[1-(3-Amino-propyl)-5-bromo-1H-indol-3-yl]-5H-1,3-dioxa-5,8-diaza-cyclopenta[b]naphthalen-6one acetic acid salt FAB-MS: m/z 441.0, 443.0 [MH+]

Example 174

7-[1-(3-Amino-propyl)-2-ethyl-1H-indol-3-yl]-5H-1,3-dioxa-5,8-diaza-cyclopenta[b]naphthalen-6-one acetic acid salt FAB-MS: m/z 391.4 [MH+]

Example 175

7-[1-(4-Amino-butyl)-2-benzyl-1H-indol-3-yl]-5H-1,3-dioxa-5,8-diaza-cyclopenta[b]naphthalen-6-one acetic acid salt FAB-MS: m/z 467.5 [MH+]

Example 176

7-[1 (6-Aminomethyl-pyridin-2-ylmethyl)-1H-indol-3-yl]-5H-1,3-dioxa-5,8-diaza-cyclopenta[b]naphthalen-6-one acetic acid salt FAB-MS: m/z 426.5 [MH+]

Example 177

7-[1-(4-Aminomethyl-benzyl)-1H-indol-3-yl]-5H-1,3-dioxa-5,8-diaza-cyclopenta[b]naphthalen-6-one acetic acid salt FAB-MS: m/z 425.5 [MH+]

Example 178

7-[1-(3-Aminomethyl-benzyl)-1H-indol-3-yl]-5H-1,3-dioxa-5,8-diaza-cyclopenta[b]naphthalen-6-one acetic acid salt FAB-MS: m/z 425.5 [MH+]

Example 179

7-[1-(4-Amino-butyl)-1H-indol-3-yl]-5H-1,3-dioxa-5,8-diaza-cyclopenta[b]naphthalen-6-one acetic acid salt FAB-MS: m/z 377.4 [MH+]

Example 180

7-[1-(3-Amino-propyl)-1H-indol-3-yl]-5H-1,3-dioxa-5,8-diaza-cyclopenta[b]naphthalen-6-one acetic acid salt FAB-MS: m/z 363.4 [MH+]

Example 181

6-[1-(3-Amino-propyl)-6-benzyloxy-1H-indol-3-yl]-2,3-dihydro-8H-1,4-dioxa-5,8-diaza-phenanthren-7-one acetic acid salt FAB-MS: m/z 483.5 [MH+]

Example 182

6-[1-(3-Amino-propyl)-5-benzyloxy-1H-indol-3-yl]-2,3-dihydro-8H-1,4-dioxa-5,8-diaza-phenanthren-7-one acetic acid salt FAB-MS: m/z 483.5 [MH+]

Example 183

6-[1-(3-Amino-propyl)-5-bromo-1H-indol-3-yl]-2,3-dihydro-8H-1,4-dioxa-5,8-diaza-phenanthren-7-one acetic acid salt FAB-MS: m/z 455.0, 457.0 [MH+]

Example 184

6-[1-(3-Amino-propyl)-2-ethyl-1H-indol-3-yl]-2,3-dihydro-8H-1,4-dioxa-5,8-diaza-phenanthren-7-one acetic acid salt FAB-MS: m/z 405.5 [MH+]

Example 185

6-[1-(4-Amino-butyl)-2-benzyl-1H-indol-3-yl]-2,3-dihydro-8H-1,4-dioxa-5,8-diaza-phenanthren-7-one acetic acid salt FAB-MS: m/z 481.6 [MH+]

Example 186

6-[1-(6-Aminomethyl-pyridin-2-ylmethyl)-1H-indol-3-yl]-2,3-dihydro-8H-1,4-dioxa-5,8-diaza-phenanthren-7-one acetic acid salt FAB-MS: m/z 440.5 [MH+]

Example 187

6-[1-(4-Aminomethyl-benzyl)-1H-indol-3-yl]-2,3-dihydro-8H-1,4-dioxa-5,8-diaza-phenanthren-7-one acetic acid salt FAB-MS: m/z 439.5 [MH+]

Example 188

6-[1-(3-Aminomethyl-benzyl)-1H-indol-3-yl]-2,3-dihydro-8H1,4dioxa-5,8-diaza-phenanthren-7-one acetic acid salt FAB-MS: m/z 439.5 [MH+]

Example 189

6-[1-(4-Amino-butyl)-1H-indol-3-yl]-2,3-dihydro-8H-1,4-dioxa-5,8-diaza-phenanthren-7-one acetic acid salt FAB-MS: m/z 391.4 [MH+]

Example 190

6-[1-(3-Amino-propyl)-1H-indol-3-yl]-2,3-dihydro-8H-1,4-dioxa-5,8-diaza-phenanthren-7-one acetic acid salt FAB-MS: m/z 377.4 [MH+]

Example 191

6-Acetyl-2-[1-(3-amino-propyl)-6-benzyloxy-1H-indol-3-yl]-4,6,7,8-tetrahydro-pyrrolo[2,3-g]quinoxalin-3-one acetic acid salt FAB-MS: m/z 508.6 [MH+]

Example 192

6-Acetyl-2-[1-(3-amino-propyl)-5-bromo-1H-indol-3-yl]-4,6,7,8-tetrahydro-pyrrolo[2,3-g]quinoxalin-3-one acetic acid salt FAB-MS: m/z 480.0, 482.0 [MH+]

Example 193

6-Acetyl-2-[1-(3-amino-propyl)-2-ethyl-1H-indol-3-yl]-4,6,7,8-tetrahydro-pyrrolo[2,3-g]quinoxalin-3-one acetic acid salt FAB-MS: m/z 430.5 [MH+]

Example 194

6-Acetyl-2-[1-(4amino-butyl)-2-benzyl-1H-indol-3-yl]-4,6,7,8-tetrahydro-pyrrolo[2,3-g]quinoxalin-3-one acetic acid salt FAB-MS: m/z 506.6 [MH+]

Example 195

6-Acetyl-2-[1-(aminomethyl-pyridin-2-ylmethyl)-1H-indol-3-yl]-4,6,7,8-tetrahydro-pyrrolo[2,3-g]quinoxalin-3-one acetic acid salt FAB-MS: m/z 465.5 [MH+]

Example 196

6-Acetyl-2-[1-(4aminomethyl-benzyl)-1H-indol-3-yl]-4,6,7,8-tetrahydro-pyrrolo[2,3-g]quinoxalin-3-one acetic acid salt FAB-MS: m/z 464.5 [MH+]

Example 197

6-Acetyl-2-[1-(3-aminomethyl-benzyl)-1H-indol-3-yl]-4,6,7,8-tetrahydro-pyrrolo[2,3-g]quinoxalin-3-one acetic acid salt FAB-MS: m/z 464.5 [MH+]

Example 198

6-Acetyl-2-[1-(4amino-butyl)-1H-indol-3-yl]-4,6,7,8-tetrahydro-pyrrolo[2,3-g]quinoxalin-3-one acetic acid salt FAB-MS: m/z 416.5 [MH+]

Example 199

6-Acetyl-2-[1-(3-amino-propyl)-1H-indol-3-yl]-4,6,7,8-tetrahydro-pyrrolo[2,3-g]quinoxalin-3-one acetic acid salt FAB-MS: m/z 402.5 [MH+]

Example 200

3-[1-(3-Aminomethyl-benzyl)-5-bromo-1H-indol-3-yl]-1H-benzo[g]quinoxalin-2-one acetic acid salt FAB-MS: m/z 509.0 [MH+]

Example 201

3-[1-(3-Amino-propyl)-2-(4-chloro-phenyl)-1H-indol-3-yl]-1H-benzo[g]quinoxalin-2-one acetic acid salt FAB-MS: m/z 479.3 [MH+]

Example 202

{3-[1-(3-Amino-propyl)-1H-indol-3-yl]-2-oxo-2H-benzo[g]quinoxalin-1-yl}-acetic acid methyl ester trifluoroacetic acid salt FAB-MS: m/z 441.1 [MH+]

Example 203

3-[1-(3-Amino-propyl)-1H-indol-3-yl]-1-ethyl-1H-benzo[g]quinoxalin-2-one acetic acid salt FAB-MS: m/z 397.1 [MH+]

Example 204

3-[5-(3-Aminomethyl-benzyl)-5H-[1,3]dioxolo[4,5-f]indol-7-yl]-6,7,8,9-tetrahydro-1H-benzo[g]quinoxalin-2-one acetic acid salt FAB-MS: m/z 479.6 [MH+]

Example 205

3-[1-(3-Amino-propyl)-5-benzyloxy-1H-indol-3-yl]-1H-benzo[g]quinoxalin-2-one acetic acid salt FAB-MS: m/z 475.2 [MH+]

Example 206

3-[1-(2-Amino-ethyl)-1H-indol-3-yl]-1H-benzo[g]quinoxalin-2-one acetic acid salt FAB-MS: m/z 355.1 [MH+]

Example 207

3-[1-(3-Hydroxy-propyl)-1H-indol-3-yl]-1H-benzo[g]quinoxalin-2-one

FAB-MS: m/z 370.1 [MH+]

Example 208

2-{3-[3-(3-Oxo-3,4-dihydro-benzo[g]quinoxalin-2-yl)-indol-1-yl]-propyl}-isothiourea tris methanesufonic acid salt FAB-MS: m/z 428.1 [MH+]

Example 209

3-[1-(3-Amino-propyl)-5-methoxy-1H-indol-3-yl]-1H-benzo[g]quinoxalin-2-one acetic acid salt FAB-MS: m/z 399.1 [MH+]

Example 210

3-[1-(3-Amino-propyl)-6-nitro-1H-indol-3-yl]-1H-benzo[g]quinoxalin-2-one acetic acid salt FAB-MS: m/z 414.4 [MH+]

Example 211

3-[1-(3-Amino-propyl)-2-ethyl-1H-indol-3-yl]-1H-benzo[g]quinoxalin-2-one acetic acid salt FAB-MS: m/z 397.1 [MH+]

Example 212

3-[1-(3-Amino-propyl)-6-benzyloxy-1H-indol-3-yl]-1H-benzo[g]quinoxalin-2-one acetic acid salt FAB-MS: m/z 475.1 [MH+]

Example 213

3-[1-(3-Amino-propyl)-2-methyl-1H-indol-3-yl]-1H-benzo[g]quinoxalin-2-one acetic acid salt FAB-MS: m/z 383.3 [MH+]

Example 214

3-[1-(3-Amino-propyl)-7-ethyl-1H-indol-3-yl]-1H-benzo[g]quinoxalin-2-one acetic acid salt FAB-MS: m/z 397.5 [MH+]

Example 215

3-[5-(3-Amino-propyl)-5H-[1,3]dioxolo[4,5-f]indol-7-yl]-1H-benzo[g]quinoxalin-2-one acetic acid salt FAB-MS: m/z 413.0 [MH+]

Example 216

7-[1-(3-Amino-propyl)-7-ethyl-1H-indol-3-yl]-2,3-dihydro-5H-1,4-dioxa-5,8-diaza-anthracen-6-one acetic acid salt FAB-MS: m/z 405.5 [MH+]

Example 217

3-[5-(3-Aminomethyl-benzyl)-5H-[1,3]dioxolo[4,5-f]indol-7-yl]-1H-benzo[g]quinoxalin-2-one acetic acid salt FAB-MS: m/z 475.0 [MH+]

Example 218

3-(8-Aminomethyl-6,7,8,9-tetrahydro-pyrido[1,2-a]indol-10-yl)-1H-benzo[g]quinoxalin-2-one acetic acid salt FAB-MS: m/z 395.1 [MH+]

Example 219

2-[1-(3-Amino-propyl)-7-ethyl-1H-indol-3-yl]-4H-benzo[f]quinoxalin-3-one acetic acid salt FAB-MS: m/z 397.5 [MH+]

Example 220

7-[1-(3-Amino-propyl)-7-ethyl-1H-indol-3-yl]-1,5-dihydro-imidazo[4,5-g]quinoxalin-6-one acetic acid salt FAB-MS: m/z 387.5 [MH+]

Example 221

7-[1-(3-Amino-propyl)-7ethyl-1H-indol-3-yl]-1,5-dihydro-1,2,5,8-tetraaza-cyclopenta[b]naphthalen-6-one acetic acid salt FAB-MS: m/z 387.5 [MH+]

Example 222

7-[1-(3-Amino-propyl)-7-ethyl-1H-indol-3-yl]-2-hydroxy-1,5-dihydro-imidazo[4,5-g]quinoxalin-6-one acetic acid salt FAB-MS: m/z 403.5 [MH+]

Example 223

3-[1-(3-Amino-propyl)-7-ethyl-1H-indol-3-yl]-1H-pyrazino[2,3-g]quinoxalin-2-one acetic acid salt FAB-MS: m/z 399.5 [MH+]

Example 224

3-[1-(3-Amino-propyl)-7ethyl-1H-indol-3-yl]-7,8-dimethyl-1H-pyrazino[2,3-g]quinoxalin-2one acetic acid salt FAB-MS: m/z 427.5 [MH+]

Example 225

3-[1-(3-Amino-propyl)-7-ethyl-1H-indol-3-yl]-1,6,7,8-tetrahydro-cyclopenta[g]quinoxalin-2-one acetic acid salt FAB-MS: m/z 387.5 [MH+]

Example 226

7-[1-(3-amino-propyl)-7-ethyl-1H-indol-3-yl]-5H-1,3-dioxa-5,8-diaza-cyclopenta[b]naphthalen-6-one acetic acid salt FAB-MS: m/z 391.4 [MH+]

What is claimed is:

1. A compound of formula (II):

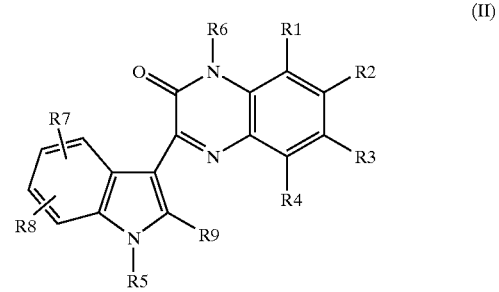

wherein:
one of: R1 and R2, R2 and R3 or R3 and R4, together form a benzene ring and the two groups of R1, R2, R3 and R4 not forming a ring, are H;

R5 is H, $C_{1-6}$ alkyl, hydroxy$C_{1-6}$ alkyl, amino$C_{1-6}$ alkyl, (amino$C_{1-3}$ alkylphenyl)$C_{1-3}$ alkyl, amidinothio$C_{1-6}$ alkyl, or (amino$C_{1-3}$ alkylpyridyl)$C_{1-3}$alkyl;

R6 is H, $C_{1-6}$ alkyl, phenyl$C_{1-6}$ alkyl, or ($C_{1-6}$ alkoxycarbonyl)$C_{1-6}$ alkyl;

R7 and R8 are each independently H, dibenzylamino, nitro, hydroxy, halogen, $C_{1-6}$alkoxy, phenyl$C_{1-6}$ alkoxy, $C_{1-6}$ alkyl or carboxy $C_{1-6}$ alkyl ester;

R9 is H, $C_{1-6}$ alkyl, phenyl, halophenyl, or benzyl;

and salts thereof;

with the proviso that:
3-[3-(3-Oxo-3,4-dihydro-benzo[g]quinoxalin-2-yl)-indol-1-yl]-propyl ammonium acetate is excluded from compounds of formula (II).

2. A compound according to claim 1, wherein R5 carries an amino group.

3. A compound according to claims 1 or 2, wherein R2 and R3 together form a benzene ring.

4. A compound according to claims 1, 2, wherein R6 is H or $C_{1-6}$ alkyl.

5. A compound according to claim 2, wherein R5 is aminoC$_{1-6}$ alkyl.

6. A compound selected from the group consisting of:
3-[1-(3-Amino-propyl)-1H-indol-3-yl]-1-benzyl-1H-benzo[g]quinoxalin-2-one trifluoroacetic acid salt,
1-(3-Amino-propyl)-3-(3-oxo-3,4-dihydro-benzo[g]quinoxalin-2-yl)-1H-indole-5-carboxylic acid methyl ester acetic acid salt,
3-[1-(3-Aminomethyl-benzyl)-5-bromo-1H-indol-3-yl]-1H-benzo[g]quinoxalin-2-one acetic acid salt,
{3-[1-(3-Amino-propyl)-1H-indol-3-yl]-2-oxo-2H-benzo[g]quinoxalin-1-yl}-acetic acid methyl ester trifluoroacetic acid salt,
3-[1-(3-Amino-propyl)-1H-indol-3-yl]-1-ethyl-1H-benzo[g]quinoxalin-2-one acetic acid salt,
3-[1-(2-Amino-ethyl)-1H-indol-3yl]-1H-benzo[g]quinoxalin-2-one acetic acid salt,
2-{3-[3-(3-Oxo-3,4-dihydro-benzo[g]quinoxalin-2-yl)-indol-1-yl]-propyl}-isothiourea tris methanesulfonic acid salt,
3-[1-(3-Aminomethyl-benzyl)-1H-indol-3-yl]-1,6,7,8-tetrahydro-cyclopenta[g]quinoxalin-2-one acetic acid salt,
7-[1-(3-Amino-propyl)-1H-indol-3-yl]-1,5-dihydro-1,2,5,8-tetraaza-cyclopenta[b]naphthalene-6-one acetic acid salt,
7-[1-(3-Amino-propyl)-5-bromo-1H-indol-3-yl]-1,5-dihydro-1,2,5,8-tetraaza-cyclopenta[b]naphthalene-6-one acetic acid salt,
7-[1-(3-Amino-propyl)-5-benzyloxy-1H-indol-3-yl]-1,5-dihydro-1,2,5,8-tetraaza-cyclopenta[b]naphthalene-6-one acetic acid salt,
7-[1-(3-Amino-propyl)-5-bromo-1H-indol-3-yl]-2,3-dihydro-5H-1,4-dioxa-5,8-diaza-anthracen-6-one acetic acid salt,
2-[1-(4-Amino-butyl)-1H-indol-3-yl]-4H-benzo[f]quinoxalin-3-one acetic acid salt,
2-[1-(3-Aminomethyl-benzyl)-1H-indol-3-yl]-4H-benzo[f]quinoxalin-3-one acetic acid salt,
2-[1-(3-Amino-propyl)-5-bromo-1H-indol-3-yl]-4H-benzo[f]quinoxalin-3-one acetic acid salt,
3-[1-(6-Aminomethyl-pyridin-2-ylmethyl)-1H-indol-3-yl]-6,7,8,9-tetrahydro-1H-benzo[g]quinoxalin-2-one acetic acid salt,
7-[1-(3-Amino-propyl)-2-methyl-1H-indol-3-yl]-2-hydroxy-1,5-dihydro-imidazo[4,5-g]quinoxalin-6-one acetic acid salt,
2-[1-(3-Amino-propyl)-5-methoxy-1H-indol-3-yl]-4H-benzo[f]quinoxalin-3-one acetic acid salt,
or a free amine thereof or a pharmaceutically acceptable salt thereof.

7. A compound of claim 1, said compound being 3-[1-(3-amino-propyl)-1H-indol-3-yl]-1-benzyl-1H-benzo[g]quinoxalin-2-one trifluoroacetic acid salt.

8. A process for the preparation of a compound of formula (II) as claimed in claim 1;
wherein R5 carries an amino or hydroxy group, comprising:
a) deprotecting a compound of formula (III) corresponding to formula (II) but in which R5 carries a protected amino or hydroxy group, or
b) converting:
i) a compound of formula (II), in which R5 carries an amino group to a salt thereof, or vice versa; or
ii) a salt of a compound of formula (II) into a different salt; or
wherein R6 is hydrogen, by reacting a compound of formula (IV):

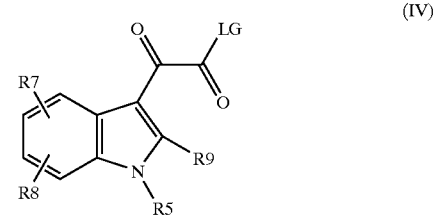

wherein,
R5, R7, R8, and R9 are as defined in formula (II) and LG is a leaving group, with a compound of formula (V):

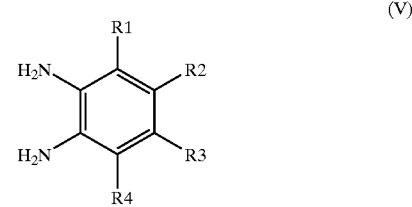

wherein one of: R1 and R2, R2 and R3 or R3 and R4, together form a benzene ring and the two groups of R1, R2, R3 and R4 not forming a ring, are H; or
wherein R6 is other than H, by reacting a compound of formula (III) which corresponds to formula (II), but in which R6 is H, with an alkylating agent in the presence of a base.

9. The process of claim 8, wherein the compound is 3-[1-(3-amino-propyl)-1H-indol-3-yl]-1-benzyl-1H-benzo[g]quinoxalin-2-one trifluoroacetic acid salt.

10. A pharmaceutical composition comprising a compound according to claim 1 together with a pharmaceutically acceptable adjuvant, diluent or carrier.

11. The pharmaceutical composition of claim 10, wherein the compound is 3-[1-(3-amino-propyl)-1H-indol-3-yl]-1-benzyl-1H-benzo[g]quinoxalin-2-one trifluoroacetic acid salt.

* * * * *